United States Patent
Nakashima

(10) Patent No.: US 7,349,520 B2
(45) Date of Patent: Mar. 25, 2008

(54) X-RAY CT SCANNER AND IMAGE-DATA GENERATING METHOD

(75) Inventor: Shigeyuki Nakashima, Yaita (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 10/986,002

(22) Filed: Nov. 12, 2004

(65) Prior Publication Data
US 2005/0105678 A1    May 19, 2005

(30) Foreign Application Priority Data
Nov. 13, 2003    (JP)    ............................ 2003-384037

(51) Int. Cl.
*A61B 6/03* (2006.01)
(52) U.S. Cl. ........................................................ 378/4
(58) Field of Classification Search .................... 378/4, 378/8, 10, 15, 19, 20, 901
See application file for complete search history.

(56) References Cited

U.S. PATENT DOCUMENTS

| | | | | |
|---|---|---|---|---|
| 6,078,639 | A | * | 6/2000 | Heuscher ...................... 378/15 |
| 6,343,108 | B1 | * | 1/2002 | Heuscher ....................... 378/4 |
| 6,754,297 | B2 | * | 6/2004 | James ............................ 378/4 |
| 2003/0072406 | A1 | * | 4/2003 | Yang .............................. 378/4 |
| 2003/0128801 | A1 | * | 7/2003 | Eisenberg et al. ............ 378/19 |
| 2004/0066879 | A1 | * | 4/2004 | Machida ........................ 378/4 |

* cited by examiner

*Primary Examiner*—Edward J. Glick
*Assistant Examiner*—Anastasia S. Midkiff
(74) *Attorney, Agent, or Firm*—Oblon, Spivak, McClelland, Maier & Neustadt, P.C.

(57) ABSTRACT

An X-ray CT scanner includes a projection-data acquisition unit for acquiring projection data for the three-dimensional region of a subject, an input unit for setting a section in a desired direction in the three-dimensional region in accordance with the instruction of an operator, a reconstruction-region calculation circuit for specifying a plurality of reconstruction portions intersecting the set section, a reconstruction arithmetic circuit for reconstructing a plurality of partial images for the specified reconstruction portions on the basis of the projection data, and an image-data processing circuit for generating an image for the set section on the basis of the plurality of reconstructed partial images.

11 Claims, 11 Drawing Sheets

X-RAY CT SCANNER AND IMAGE-DATA GENERATING METHOD

CROSS-REFERENCE TO RELATED APPLICATIONS

This application is based upon and claims the benefit of priority from prior Japanese Patent Application No. 2003-384037, filed Nov. 13, 2003, the entire contents of which are incorporated herein by reference.

BACKGROUND OF THE INVENTION

1. Field of the Invention

The present invention relates to an X-ray CT scanner and, particularly, it relates to an X-ray CT scanner and an image-data generating method capable of efficiently generating image data in a desired image section.

2. Description of the Related Art

High-speed and high-performance X-ray detectors and processors have allowed recent X-ray CT scanners to display CT images in slice planes (sections orthogonal to the body axis of a subject) in real time owing to a high-speed image reconstruction which is executed in parallel with acquisition of X-ray projection data.

Furthermore, the use of two-dimensional X-ray detector in which multiple X-ray detecting elements are disposed not only in a scanning direction (the rotating direction of the frame) but also in a slice direction (in the direction of the body axis of a subject) allows practical application of multislice CT scanners capable of acquiring X-ray projection data (hereinafter, referred to as projection data) in multiple slice planes and generating image data in the slice planes (axial image data) substantially at the same time.

On the other hand, in order to obtain image data in a desired section other than the axial image data, the diagnostic region of the subject is shifted along the body axis to generate multiple axial image data or three-dimensional volume data by using acquired projection data, from which image data (what is called multi-planar reconstruction (MPR) image data) in the desired image section is generated. (For example, refer to JP-A-2003-116838, pp. 11-12, FIGS. 9-10)

It is not easy to grasp three-dimensional information in the diagnostic region of a subject from multiple axial image data. Accordingly, MPR image data in an optimum section for the diagnostic region has conventionally been generated on the basis of the axial image data, as has been described above. In that case, multiple axial image data in the diagnostic region must be combined first to generate three-dimensional image data. This requires much time to generate the three-dimensional image data, making it difficult to generate MPR image data in a short time, which results in not only decreasing diagnostic efficiency but also placing a heavy load on the operator.

On the other hand, decreasing the number of pixels of the axial image data or increasing slicing distance can decrease the time required to generate three-dimensional image data. However, also the pixels of MPR image data generated from the acquired three-dimensional image data are roughened and so low-resolution MPR image data is generated. Briefly, the resolution of an image and image-data generation time are in trade-off relationship, which were not satisfied at the same time.

BRIEF SUMMARY OF THE INVENTION

It is an object of the present invention to provide an X-ray CT scanner and an image-data generation method capable of generating high-resolution MPR image data in a short time.

An X-ray CT scanner according to a first aspect of the present invention includes: a device configured to acquire projection data for the three-dimensional region of a subject; a device configured to set a section in a desired direction in the three-dimensional region in accordance with the instruction of an operator; a device configured to specify a plurality of reconstruction portions intersecting the set section; a reconstruction device configured to reconstructing a plurality of partial images for the specified reconstruction portions on the basis of the projection data; and a device configured to generate an image for the set section on the basis of the plurality of reconstructed partial images.

An X-ray CT scanner according to a second aspect of the invention includes: a device configured to acquire projection data for the three-dimensional region of a subject; a positioning-image generation device configured to generate a plurality of positioning images on the basis of the acquired projection data; a display device configured to display the positioning images; a section setting device configured to set a section in a desired direction on the displayed positioning images in accordance with the instruction of an operator; a device configured to specify a plurality of reconstruction portions intersecting the set section; a device configured to generate a plurality of partial images for the plurality of reconstruction portions on the basis of the projection data; and a device configured to generate an image for the section on the basis of the plurality of partial images.

An X-ray CT scanner according to a third aspect of the invention includes: a device configured to continuously acquire projection data for the three-dimensional region of a subject; a device configured to set a section in a desired direction in the three-dimensional region in accordance with the instruction of an operator; a device configured to specify a plurality of reconstruction portions intersecting the set section; a reconstruction device configured to continuously reconstruct a plurality of partial images for the specified reconstruction portions on the basis of the projection data; and a device configured to continuously generate images for the set section on the basis of the plurality of reconstructed partial images; and a display device configured to display the images continuously.

An image generation apparatus according to a fourth aspect of the invention includes: a device configured to set a section in a desired direction in the three-dimensional region of a subject in accordance with the instruction of an operator; a device configured to specify a plurality of reconstruction portions intersecting the set section; a reconstruction device configured to reconstruct a plurality of partial images for the specified reconstruction portions on the basis of the projection data for the three-dimensional region; and a device configured to generate an image for the set section on the basis of the plurality of reconstructed partial images.

An image generation apparatus according to a fifth aspect of the invention includes: An image generation apparatus comprising: a positioning-image generation device configured to generate a plurality of positioning images on the basis of projection data for the three-dimensional region of a subject; a display device configured to display the positioning images; a section setting device configured to set a section in a desired direction on the displayed positioning images in accordance with the instruction of an operator; a device configured to specify a plurality of reconstruction portions intersecting the set section; a device configured to generate a plurality of partial images for the plurality of reconstruction portions on the basis of the projection data; and a device configured to generate an image for the section on the basis of the plurality of partial images.

A method for generating image data, according to a sixth aspect of the invention, includes extracting projection data of a specified slice plane(s) from projection data in a plurality of slice planes for a subject; generating a positioning image on the basis of the extracted projection data; displaying the positioning image; specifying a plurality of reconstruction portions intersecting a section set in a desired direction on the displayed positioning image; reconstructing a plurality of partial images for the plurality of reconstruction portions on the basis of the acquired projection data; and generating an image for the set section from the plurality of reconstructed partial images.

A method for generating image data, according to a seventh aspect of the invention, includes acquiring continuously projection data for the three-dimensional region of a subject; reconstructing continuously a plurality of partial images for a plurality of reconstruction portions intersecting a set section in accordance with the instruction of an operator; generating continuously images for the set section on the basis of the plurality of reconstructed partial images; and displaying the images continuously.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will be described hereinbelow with reference to the drawings.

First Embodiment

An X-ray CT scanner 100 according to a first embodiment of the present invention includes a multislice X-ray detector having multiple X-ray detecting elements arranged in two dimensions. For example, projection data of 320 slices (first projection data) for the three-dimensional region of a subject are acquired at first slicing intervals of $\Delta Z1$. For example, discrete projection data of 32 slices (second projection data) are extracted from the acquired projection data of 320 slices at second slice intervals of $\Delta Z2$ ($\Delta Z2 > \Delta Z1$). 32-slices of tomographic images are reconstructed from the extracted second projection data. The 32-slices of tomographic images which have low resolution in the slice direction are used as positioning images for an operator to set the position and direction of the section (oblique plane) of a high-resolution tomographic image (MPR image). A section in a desired position and direction is set on multiple positioning images. 320 portions corresponding to the positions where the set oblique plane and the 320 slices with the first slicing intervals intersect each other are reconstructed. Portions other than said portions are not reconstructed. The 320 reconstructed partial images are connected together and interpolated as necessary to generate a high-resolution tomographic image (MPR image) for the oblique plane.

(Structure of the Scanner)

Figure 1:
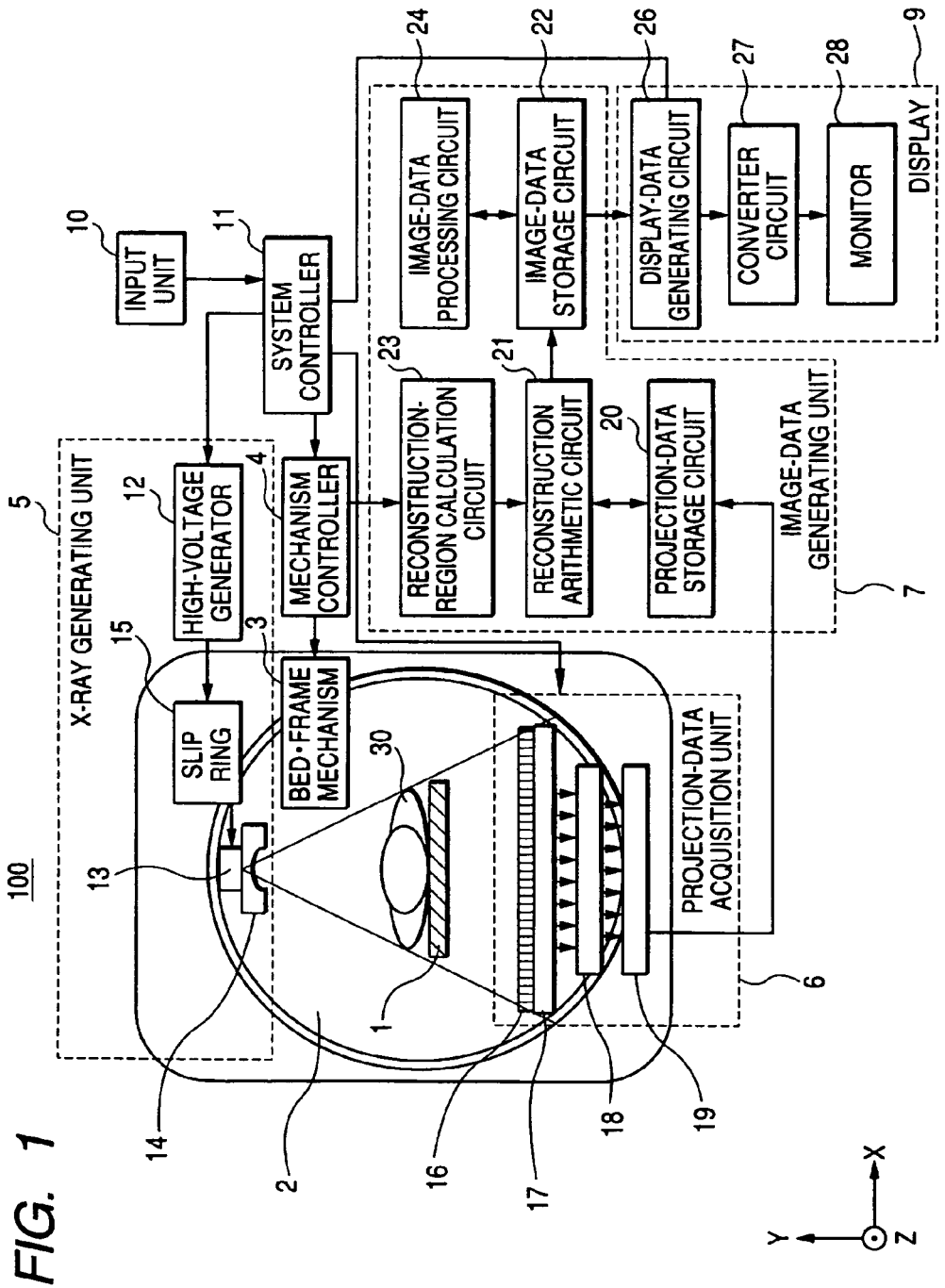
FIG. 1 is a block diagram showing the structure of the entire X-ray CT scanner according to a first embodiment of the present invention.

Referring to FIGS. 1 and 2, the structure of the X-ray CT scanner 100 according to the first embodiment will be described. FIG. 1 is a block diagram showing the structure of the entire X-ray CT scanner 100 according to this embodiment. The X-ray CT scanner 100 includes a bed 1 which mounts a subject 30 and is inserted into the opening of a frame rotating unit 2, to be described later, the frame rotating unit 2 rotating around the subject 30, and a bed and frame mechanism 3 for moving and rotating the bed 1 and the frame rotating unit 2, respectively, and further includes a mechanism controller 4 for controlling the bed frame mechanism 3, an X-ray generating unit 5 for applying X-rays to the subject 30, and a projection-data acquisition unit 6 for acquiring data for X-rays that have passed through the subject 30.

The X-ray CT scanner 100 includes an image-data generating unit 7 for reconstructing the projection data acquired by the projection-data acquisition unit 6 to generate image data, a display 9 for displaying the generated image data, an input unit 10 for inputting exposure conditions etc., and a system controller 11 for controlling over the foregoing units.

The bed 1 includes a tabletop which can be slid along the length thereof by driving the bed-frame mechanism 3, on which the subject 30 is generally placed such that the body axis agrees substantially with the length of the tabletop. The mechanism controller 4 controls the movement of the tabletop along the long axis of the bed 1 and the rotation speed of the frame rotating unit 2 by the control signals from the system controller 11.

The X-ray generating unit 5 includes an X-ray tube 13 for emitting X-rays onto the subject 30, a high-voltage generator 12 for generating high voltage to be applied between the positive electrode and the negative electrode of the X-ray tube 13, an X-ray limiting device 14 for collimating the X-ray emitted from the X-ray tube 13, and a slip ring 15 for supplying power to the X-ray tube 13 mounted to the frame rotating unit 2.

The X-ray tube 13 is a vacuum tube that generates X-rays, which accelerates electrons by high voltage applied from the high-voltage generator 12 to strike them against a tungsten target, thereby generating X-rays. The X-ray limiting device 14 is located between the X-ray tube 13 and the subject 30 and has the function of limiting the X-rays emitted from the X-ray tube 13 into a specified image-reception size. For example, the X-ray limiting device 14 forms the X-rays emitted from the X-ray tube 13 into a cone beam or fan beam according to an effective field of view (FOV).

The projection-data acquisition unit 6 includes an X-ray detector 16 for detecting X-rays that have passed through the subject 30, a switch group 17 for bundling signals sent from the X-ray detector 16 into a specified number of channels, a data acquisition circuit (hereinafter, referred to as a data acquisition system (DAS)) 18 for A/D converting the signals outputted from the switch group 17, and a data transmission circuit 19 for sending the output of the DAS 18 to the image-data generating unit 7 without contact.

The X-ray tube 13, the X-ray limiting device 14, the slip ring 15, and the projection-data acquisition unit 6 are mounted on the frame rotating unit 2 which can rotate with respect to a frame fixed unit and rotates around the rotation axis parallel with the body axis (Z-axis) of the subject 30 at as high as 1 to 2 rotations per second in accordance with the drive control signal from the mechanism controller 4.

Figure 2A:
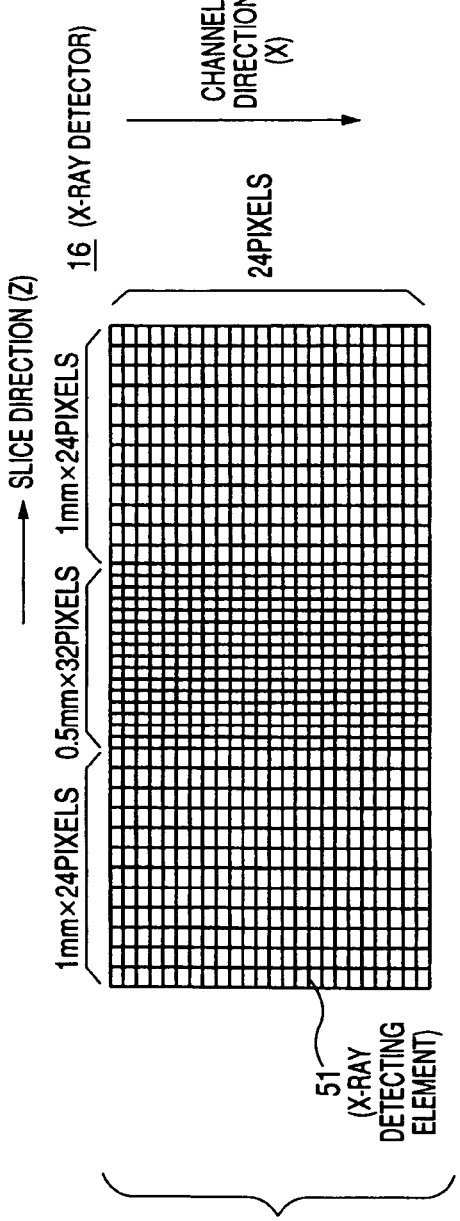
FIGS. 2A and 2B are diagrams showing the structure of an X-ray detector and a projection-data acquiring unit in the embodiment.
Figure 2B:
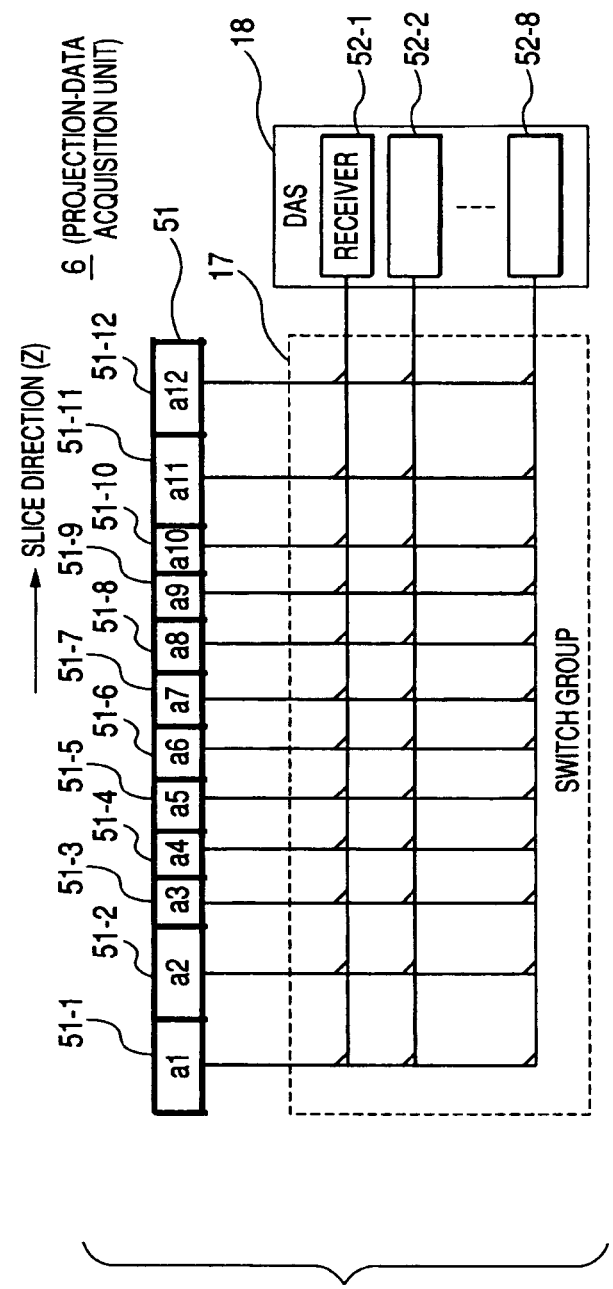

Referring to FIGS. 2A and 2B, the structure of the X-ray detector 16, the switch group 17, and the DAS 18 of the projection-data acquisition unit 6 will be described. FIG. 2A is a development plan of the X-ray detector 16 in which X-ray detecting elements 51 are arranged in two-dimensions, in which each of the X-ray detecting elements 51 includes a scintillator and a photodiode.

The multislice X-ray detector 16 includes, e.g., 80 X-ray detecting elements 51 in the slice direction (Z-direction) which is the direction of the body axis of the subject 30 and 24 X-ray detecting elements 51 in the channel direction (X-direction) orthogonal to the slice direction. The X-ray detecting elements 51 arranged in the channel direction are practically mounted to the frame rotating unit 2, along an arc with the focus of the X-ray tube 13 as the center. 32 X-ray detecting elements 51 for acquiring data having a slice thickness of 0.5 mm are disposed in the center of the slice direction of the X-ray detector 16. 24 X-ray detecting elements 51 for acquiring data having a slice thickness of 1.0 mm are disposed at the opposite ends of the 32 X-ray detecting elements 51, respectively.

Referring again to FIG. 1, when the switch group 17 of the projection-data acquisition unit 6 transfers the signals detected in the X-ray detector 16 transfers to DAS 18, it supplied the signals from the X-ray detector 51 in the slice direction, with the signals "data-bundled" to a specified number of channels.

The DAS 18 includes receive units for multiple channels. The receive units convert the current signals from the X-ray detector 16 to voltage and further convert them to digital signals with an A/D converter (not shown), thereby producing projection data.

The data transmission circuit 19 sends the projection data outputted from the DAS 18 to a projection-data storage circuit 20 of the image-data generating unit 7, to be described later, e.g., with an optical transmission means and stores it. The data transmission method may be replaced with other methods capable of transmitting signals between the rotating body and the fixed body, such as the above-described slip ring. However, the X-ray detector 16 detects enormous amounts of two-dimensional projection data during one rotation (approximately one second). Therefore, the DAS 18 and the data transmission circuit 19 are required to have a high-speed processing function to achieve such mass projection data transmission.

Figure 12:
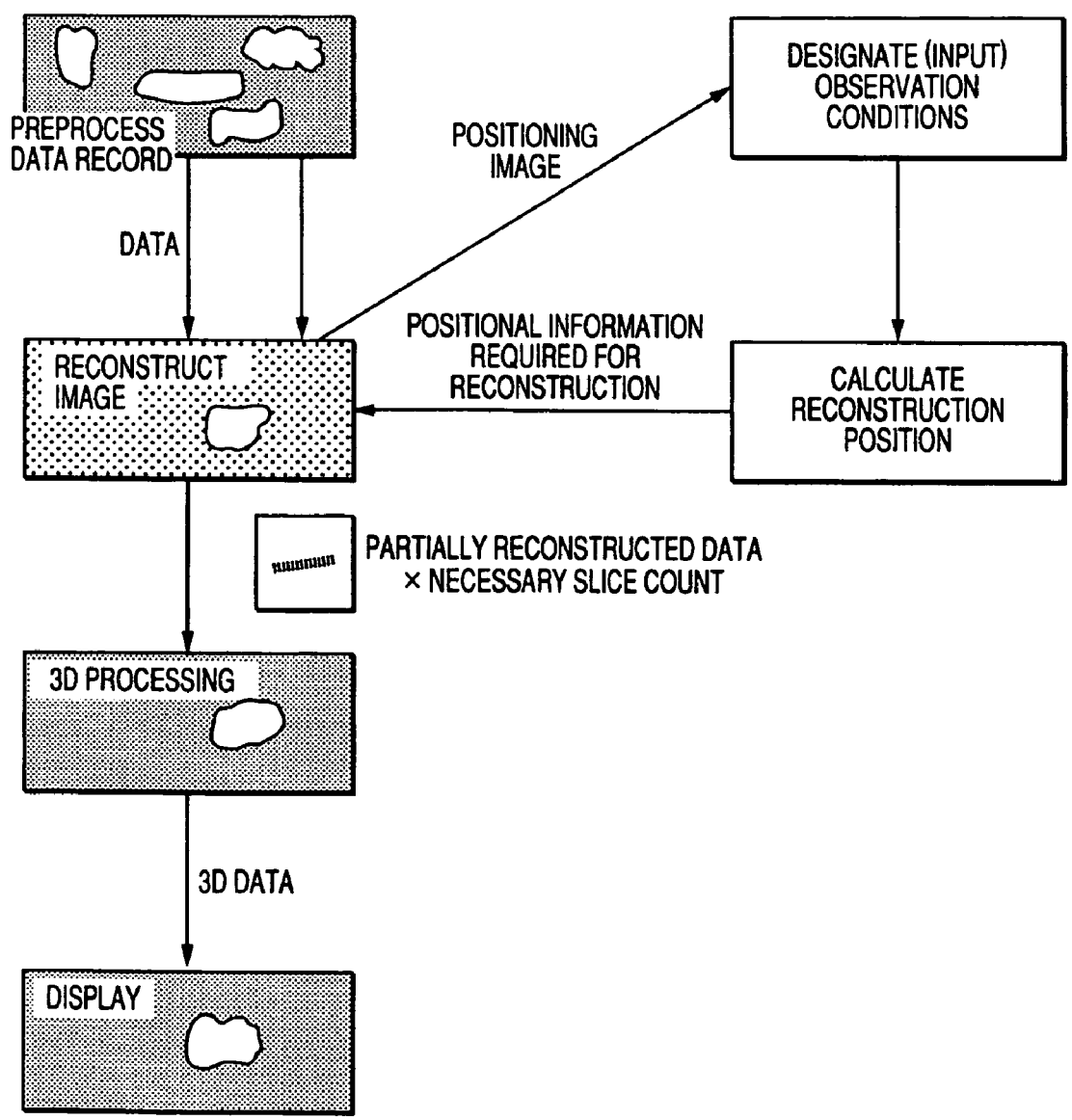
FIG. 12 is a diagram of supplementary explanation of steps S3 to S7 of FIG. 3.

Referring to FIG. 2B, the "data bundling" by the projection-data acquisition unit 6 will be described. In FIG. 2B, 12 X-ray detecting elements 51-1 to 51-12 are arranged in the slice direction in one channel of the channel direction, for the convenience of description.

In the X-ray detector 16 of FIG. 2B, for example, eight X-ray detecting elements 51-3 to 51-10 are arranged at intervals of 0.5 mm in the center of the slice direction and, four X-ray detecting elements 51-1 and 51-2 and 51-11 and 51-12 are disposed at intervals of 1 mm at opposite ends, respectively. The DAS 18 is composed of, e.g., eight receivers 52-1 to 52-8. The switch group 17 "bundles" 12 rows of signals detected by the X-ray detecting elements 51 into eight rows of data.

The "data bundling" allows a change in the thickness of the multislice. For example, connecting the X-ray detecting elements 51-3 to 51-10 to the receivers 52-1 to 52-8 of the DAS 18 via the switch group 17, respectively, allows eight slices of 0.5-mm-thick data to be provided. When 1-mm-thick data is required, the X-ray detecting element 51-1 is connected to the receiver 52-1, the X-ray detecting element 51-2 to the receiver 52-2, the X-ray detecting elements 51-3 and 51-4 to the receiver 52-3, and the X-ray detecting elements 51-5 and 51-6 to the receiver 52-4, respectively. Similarly, the X-ray detecting elements 51-7 and 51-8 are connected to the receiver 52-5, the X-ray detecting elements 51-9 and 51-10 to the receiver 52-6, the X-ray detecting element 51-11 to the receiver 52-7, and the X-ray detecting element 51-12 to the receiver 52-8, respectively.

Signals detected by the 0.5-mm-pitch X-ray detecting elements 51 of the X-ray detector 16, shown in FIG. 2A, are similarly subjected to the "data bundling" and as such, projection data equal to that when 64 X-ray detecting elements 51 with 1-mm pitches are arranged in the slice direction is acquired. Briefly, the number of equivalent detecting elements in the slice direction amounts to 64. Such "data bundling" allows applications to both of high-resolution radiography for a small region and high-sensitivity radiography for a wide region.

Referring back to FIG. 1, the image-data generating unit 7 includes the projection-data storage circuit 20, a reconstruction arithmetic circuit 21, an image-data storage circuit 22, a reconstruction-region calculation circuit 23, and an image-data processing circuit 24.

The projection-data storage circuit 20 stores projection data detected by the X-ray detector 16 and sent via the data transmission circuit 19, which stores projection data acquired for multiple slice planes of the subject 30. The reconstruction arithmetic circuit 21 reconstructs projection data (second projection data) with specified pitches which are extracted from the projection data (first projection data) stored in the projection-data storage circuit 20 to generate multiple axial image data (hereinafter, referred to as two-dimensional positioning image data) and then generates image data (hereinafter, referred to as MPR image data for convenience) for one or multiple desired image sections intersecting the two-dimensional positioning image data section using the first projection data.

The image-data processing circuit 24 interpolates data in the image planes and between the images of the multiple two-dimensional positioning images generated by the reconstruction arithmetic circuit 21 as necessary and then performs volume rendering etc., thereby generating three-dimensional positioning image data capable of highlighted display of the surfaces of the body and the organs of the subject 30.

The reconstruction-region calculation circuit 23 calculates multiple regions required to generate the MPR image of a section (oblique plane) set for the two-dimensional positioning image or the three-dimensional positioning image which is displayed on the display 9. The multiple regions include a linear region (one-dimensional region) where a data-acquisition slice plane and an oblique plane intersect each other or a region with a specified width (two-dimensional region) around the line.

The image-data storage circuit 22 stores data of the multiple two-dimensional positioning images and the MPR images which are generated by the reconstruction arithmetic circuit 21 and the three-dimensional positioning image which is generated from the two-dimensional positioning images by the image-data processing circuit 24.

The display 9 includes a display-data generating circuit 26, a converter circuit 27, and a monitor 28. The display-data generating circuit 26 stores the three-dimensional positioning image data, the MPR image data, and additional respective information on the image data in superposition state. Particularly, graphic information such as the outline of the MPR image section which is set by the input unit 10 is superposed to the three-dimensional positioning image data.

Such display data are subjected to D/A conversion and TV-format conversion by the converter circuit 27 and then displayed on the monitor 28. The use of the monitor 28 of the display 9 and the input unit 10 allows interaction between an operator and the scanner.

The input unit 10 is an interactive interface including a display panel and input devices such as a keyboard, various switches, selection buttons, and a mouse. Prior to acquisition of projection data, an operator sets various conditions such as projection-data acquisition conditions, reconstruction conditions, and image-display conditions via the input unit 10.

The projection-data acquisition conditions include an exposure region, the method of scanning, a slice interval, the number of slices, tube voltage/tube current, the size of exposure region, a scan interval, a view interval, and the moving speed of the bed 1. The scan interval is the interval of exposure time for multiple image data exposed in specified slice positions. For example, when the scan interval is two seconds and the rotation speed of the X-ray tube 13 and the X-ray detector 16 is one rotation per second, one exposure is performed every two rotations. The view interval is the interval between data acquisitions in the rotating direction of the X-ray tube 13 and the X-ray detector 16.

The reconstruction conditions include the method of reconstruction, the size of a reconstruction region, the size of reconstruction matrix, and the interval and number of image data in the slice direction, which are set for each of the two-dimensional positioning image data and MPR image data.

The image-display conditions include methods for displaying positioning image data and MPR image data and image processing method necessary for displaying the image data. For example, the method for displaying positioning image data includes surface-highlighted display of three-dimensional positioning image data, for which a volume rendering method is preferable as the image processing method.

Also the setting of the MPR image section and input of various command signals for the three-dimensional positioning image displayed on the display 9 are performed using the input device of the input unit 10.

The system controller 11 includes a CPU and a storage circuit (not shown) and temporarily stores various setting conditions and various command signals sent from the input unit 10 in the internal storage circuit. The system controller 11 exercises control over the units such as the mechanism controller 4, the X-ray generating unit 5, the projection-data acquisition unit 6, the image-data generating unit 7, and the display 9 in accordance with the instruction from the input unit 10.

(Procedure for Generating MPR Image Data)

Figure 3:
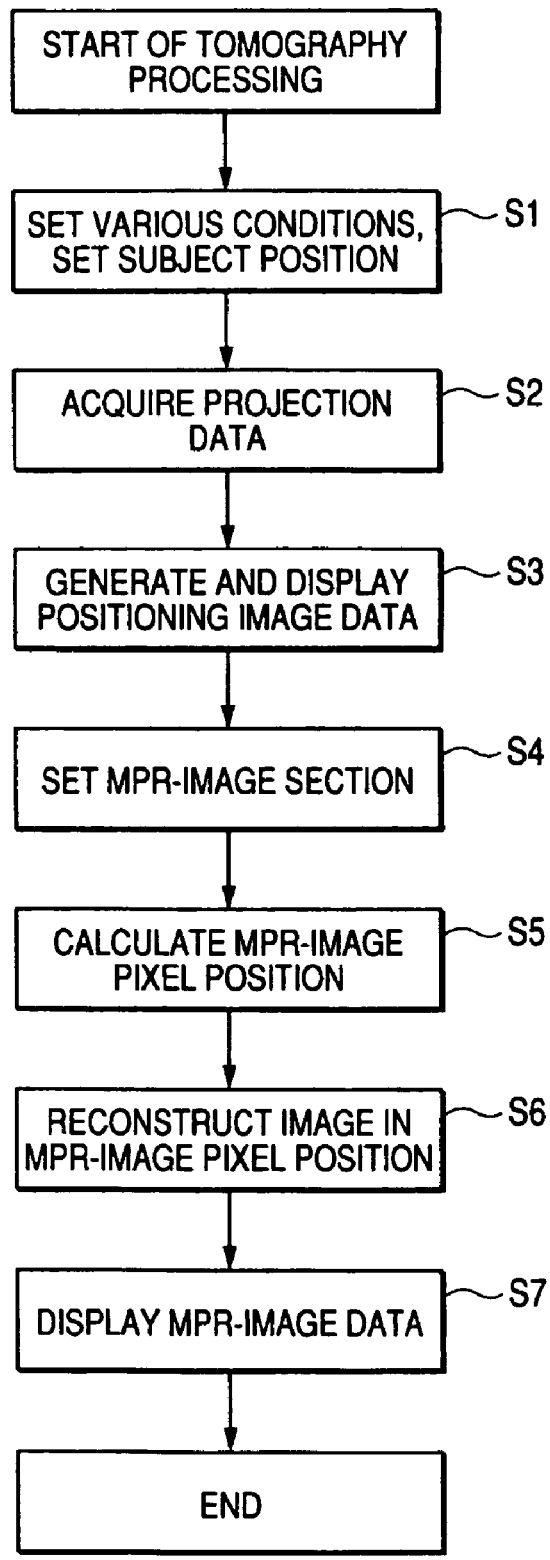
FIG. 3 is a flowchart for the procedure of generating MPR image data in the embodiment.

Referring to FIGS. 3 to 8 and 12 to 15, the procedure for generating MPR image data according to the first embodiment will be described. FIG. 3 is a flowchart of the procedure for generating MPR image data in the embodiment.

In advance of acquisition of projection data, the operator of the scanner sets the projection-data acquisition conditions, the reconstruction conditions, and the image-display conditions necessary for acquisition of projection data, image reconstruction, and image processing with the input unit 10 and then the system controller 11 stores the set conditions in the storage circuit (not shown).

Figure 4:
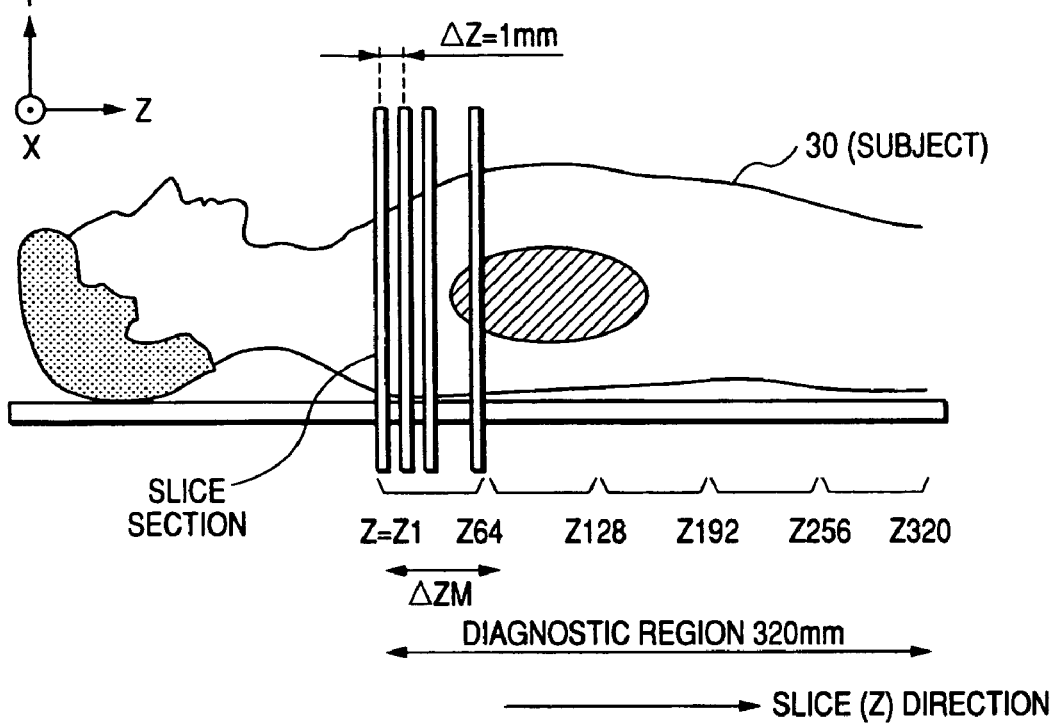
FIG. 4 is a diagram showing projection-data acquiring positions in the embodiment.

FIG. 4 shows projection-data acquiring position in the embodiment. As has been shown in FIG. 2A, this embodiment uses the X-ray detector 16 in which the X-ray detecting elements 51 are disposed in two dimensions, 24 elements in the channel direction and 80 elements 51 in the slice direction. By moving the X-ray detector 16 in the slice direction (along the body axis), a wide-region projection data can be acquired in a short time.

For example, projection data is acquired in each of multiple slice positions (Z=Z1 to Z=Z320) in which first slice intervals ΔZ1 are set to 1 mm for a diagnostic region (three-dimensional region) with a length of 320 mm in the slice direction. In that case, projection data acquired by the X-ray detector 16 rotating around the subject 30 in the initial position corresponds to 64 slices from Z=Z1 to Z=Zz64. Accordingly, projection data for the entire diagnostic region are acquired by moving the subject 30 in five steps at intervals of 64 mm in the slice direction.

After completion of the setting of the foregoing conditions, the subject 30 is placed on the tabletop of the bed 1 and then moved in the slice direction so that the frame rotating unit 2 is located in a specified position relative to the slice positions Z=Z1 to Z=Z64 (step S1).

The operator then inputs command signals for acquiring projection data and generating and displaying positioning image data with the input unit 10. The system controller 11 which has received the command signals from the input unit 10 sends a control signal to the bed-frame mechanism 3 via the mechanism controller 4 to rotate the frame rotating unit 2 to which the X-ray tube 13 and the X-ray detector 16 are mounted so as to face each other at a rate of one to two rotations per second around the subject 30, thereby acquiring projection data.

At the time of X-ray application to the subject 30, the high-voltage generator 12 supplies power (tube voltage and tube current) necessary to apply X-rays for acquiring projection data to the X-ray tube 13 in accordance with tube-voltage and tube-current setting conditions stored in the storage circuit (not shown) of system controller 11. The X-ray tube 13 receives the power and applies fan-beam X-rays to the subject 30.

The X-rays that are emitted from the X-ray tube 13 and have passed through the subject 30 are detected by the X-ray detector 16 in the projection-data acquisition unit 6. Specifically, the X-rays that have passed through the subject 30 are converted to electrical charge (current) proportional to the radiation dosage by the X-ray detector 16 which has 64 equivalent elements in the slice direction by "data bundling" and 24 elements in the channel direction. The current is further supplied to the DAS 18, where it is converted to voltage and then A/D converted to generate projection data of 64 slices.

The projection data is sent to the transmitter of the data transmission circuit 19 mounted to the frame rotating unit 2, where it is converted to an optical signal and received by the receiver of the data transmission circuit 19 mounted to the frame fixed unit through the air. The received projection data is stored in the projection-data storage circuit 20 of the image-data generating unit 7.

Such X-ray application to the subject 30 and detection of X-ray transmission data are performed while the X-ray tube 13 and the X-ray detector 16 are being rotated around the subject 30. For example, when X-rays are applied to the subject 30 at a frequency of 1000 times/rotation, projection data corresponding to 64,000/sec to 128,000/sec are acquired for 64 slices. The projection data acquired in each slice position (Z=Z1 to Z64) are stored in the projection-data storage circuit 20.

The mechanism controller 4 transmits a control signal to the bed-frame mechanism 3 in accordance with the instruction signal from the system controller 11 to move the bed 1 in the slice direction by a specified moving distance ΔZM=64 mm. Then, projection data in slice positions of Z=Z65 to Z128 are acquired according to the procedure similar to the above and are stored in the projection-data storage circuit 20. Furthermore, projection data acquired in slice positions Z=Z129 to Z192, Z=Z193 to Z256, and Z=Z257 to Z320 are stored in the projection-data storage circuit 20 and the acquisition and storage of projection data in the diagnostic region are completed (step S2).

Projection data (first projection data) for 320 slice planes with 1-mm pitches are thus acquired. In parallel with the acquisition, the system controller 11 provides positional information on the first slice position (e.g., Z=Z10) for generating positioning image data to the reconstruction arithmetic circuit 21. The reconstruction arithmetic circuit 21 reads projection data corresponding to the slice position from the projection data stored in the projection-data storage circuit 20, for example, in the range of 180 degrees+the fan-beam angle, to perform reconstruction (half reconstruction), thereby generating two-dimensional positioning image data. Furthermore, projection data (second projection data) corresponding to the second slice position (Z=Z20) to the 32nd slice position with slice intervals of 10 mm are also reconstructed to generate two-dimensional image data. Finally, 32 slices of two-dimensional positioning image are generated at slice intervals of 10 mm and stored in the image-data storage circuit 22.

The image-data processing circuit 24 then reads out 32 two-dimensional positioning image data stored in the image-data storage circuit 22. The 32 two-dimensional positioning image data are interpolated in the slice direction and combined on the basis of the image-processing set data provided from the system controller 11 and are further subjected to volume rendering to generate single three-dimensional positioning image data in which the body surface and the boundary surface of organs are highlighted. The generated three-dimensional positioning image data is stored in the image-data storage circuit 22 and displayed on the monitor 28 of the display 9 (step S3).

Figure 5:
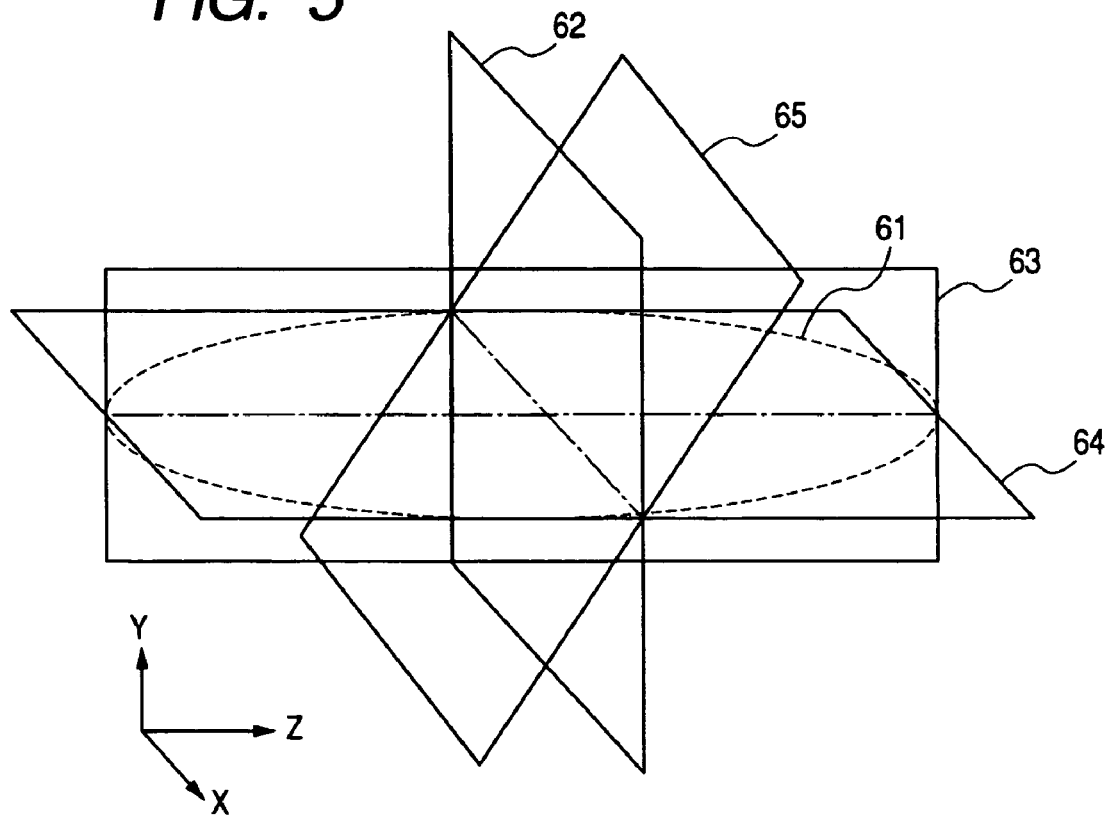
FIG. 5 is a diagram showing a method for setting MPR image sections in the embodiment.
Figure 6:
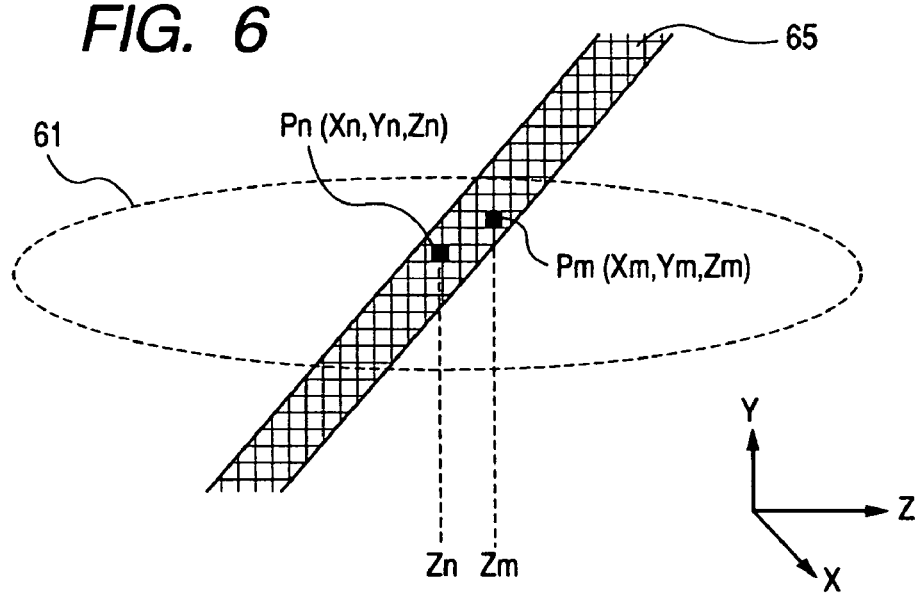
FIG. 6 is a diagram showing the relationship between the pixels of the MPR image and projection data used for the pixels in the embodiment.

The operator sets one or more MPR image sections for the three-dimensional positioning image displayed on the display 9 by using the input device of the input unit 10. FIG. 5 shows an axial section (a cross section orthogonal to the body axis of the subject 30) 62, a sagittal section (longitudinal section as viewed from the side of the subject 30) 63, a coronal section (longitudinal section as viewed from the front of the subject 30) 64, and an oblique section (oblique section of the subject 30) 65, which are set for a three-dimensional positioning image 61 of the subject 30. However, multiple oblique sections 65 can be set, in which case the positions and angles of the oblique sections 65 are set with the mouse etc. of the input unit 10 with reference to the three-dimensional positioning image 61 (step S4).

Figure 13:
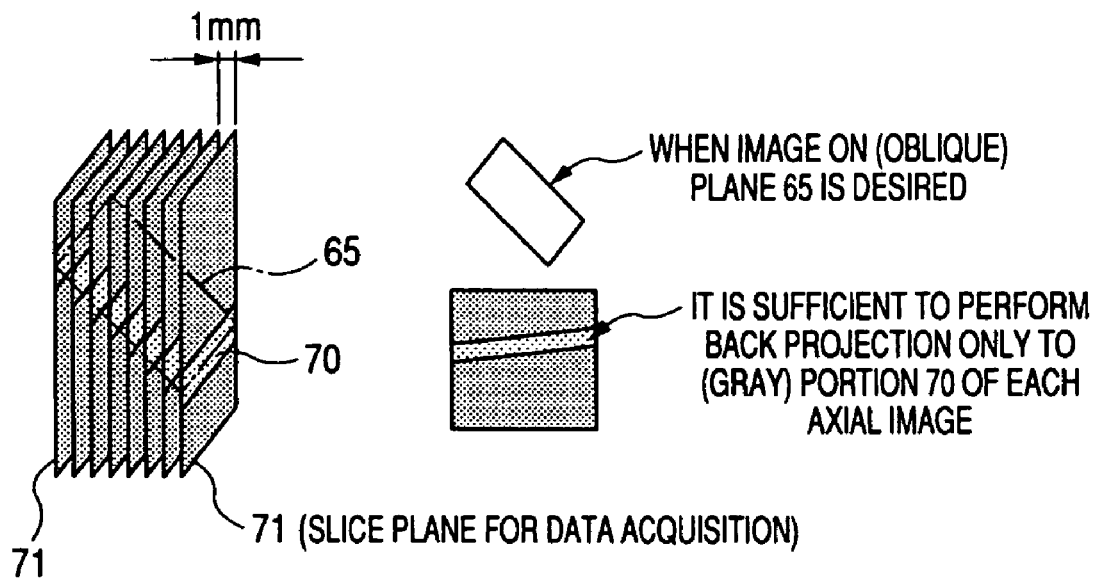
FIG. 13 is a diagram of a reconstruction position (region to be reconstructed) corresponding to the MPR plane in the embodiment.
Figure 15:
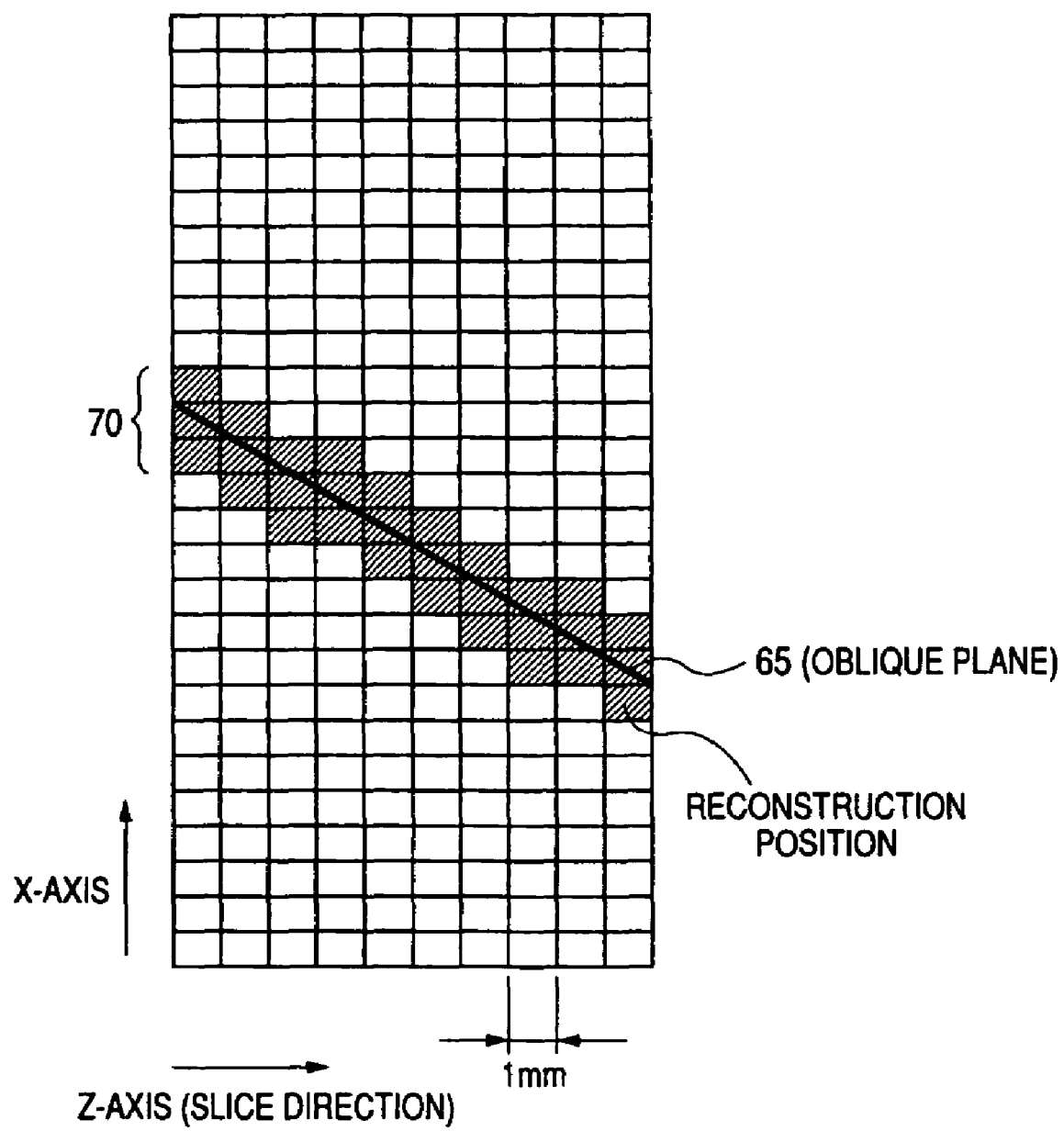
FIG. 15 is a detail view of FIG. 5.

The reconstruction-region calculation circuit 23 of the image-data generating unit 7 calculates the positions of all pixels that constructs the MPR image section (oblique section 65) set for the three-dimensional positioning image 61 and provides its positional information to the reconstruction arithmetic circuit 21 (step S5). In other words, as shown in FIGS. 13 and 15 by way of example, the reconstruction-region calculation circuit 23 determines 320 portions 70 where the set oblique section 65 and the 320 slice planes in which data is acquired intersect each other. The portion 70 may be a line (one dimension) or, alternatively, a region (two dimensions) with a specified width with its center at the line. The portion 70 in FIG. 15 has a width corresponding to three pixels.

The reconstruction arithmetic circuit 21 reconstructs each pixel in the oblique section 65 determined by the reconstruction-region calculation circuit 23. For example, when generating the MPR image data for the oblique section 65, shown in FIG. 6, reconstruction of pixels Pn (Xn, Yn, Zn) is performed by back projection to X=Xn and Y=Yn of the slice plane by using the first projection data acquired in the slice plane of Z=Zn (or a slice plane closest to Z=Zn). For a pixel Pm (Xm, Ym, Zm), X=Xm and Y=Ym of the slice plane is reconstructed by using the first projection data acquired in the slice plane of Z=Zm. Furthermore, other pixels are similarly reconstructed to generate MPR image data in the oblique section 65.

In other words, the partial image of the portion 70 in the slice plane Z1 is reconstructed from the projection data corresponding to the slice plane Z1. The slice plane Z1 is reconstructed only for the portion intersecting the oblique section 65. The portion other than the portion 70 in the slice plane Z1 is not reconstructed. Similarly, with respect to another slice plane Zn, only the partial image of the portion 70 intersecting the oblique section 65 is reconstructed.

Multiple partial images in different slice positions are combined to one MPR image corresponding to the oblique section 65. The combination process includes interpolation as necessary.

Other sections 62 to 64 which are set for the three-dimensional positioning image are also reconstructed through the similar procedure to generate MPR images. The acquired MPR image in each plane is stored in a specified storage region of the image-data storage circuit 22 (step S6).

The display-data generating circuit 26 of the display 9 reads the MPR image data stored in the image-data storage circuit 22 and generates display image data according to a specified display format. The display image data is subjected to D/A conversion and TV-format conversion by the converter circuit 27 and is then displayed on the display 9 (step S7).

Figure 7:
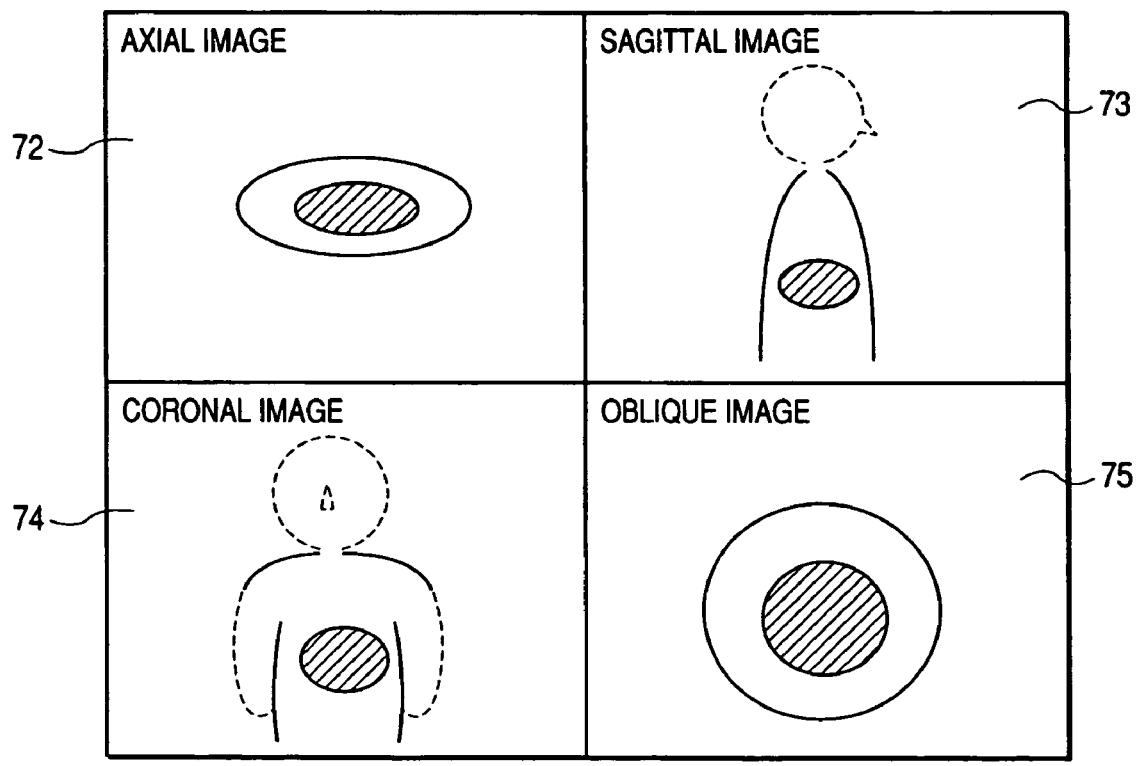
FIG. 7 is a diagram of an example of MPR images displayed on the display of the embodiment.

FIG. 7 shows a concrete example of MPR images displayed on the monitor 28 of the display 9. The four-split display screen of the monitor 28 displays, for example, an MPR image in axial section (axial image) 72, an MPR image in sagittal section (sagittal image) 73, an MPR image in coronal section (coronal image) 74, and an MPR image in oblique section (oblique image) 75.

Figure 8:
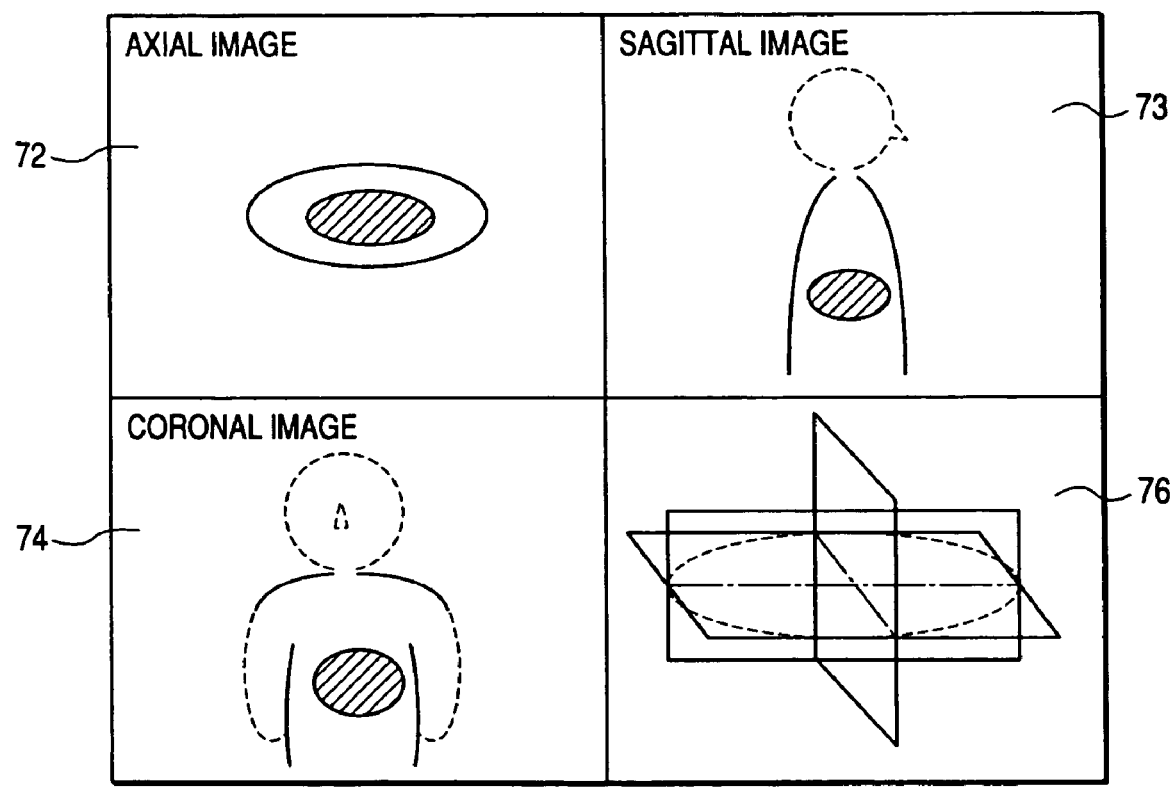
FIG. 8 is a diagram of another example of MPR images displayed on the display of the embodiment.

FIG. 8 shows another concrete example, showing a three-dimensional positioning image 76 to which MPR image sections are added, in parallel, to facilitate grasping the positional relationship between the foregoing image sections and the subject 30. It is to be understood that the number and arrangement of the MPR images displayed on the display 9 are not limited to FIGS. 7 and 8.

This embodiment can also be applied to a case in which the same diagnostic region is exposed multiple times as in observation of a contrast medium injected into a body. In such a case, after completion of generation and display of the first MPR image data, the bed 1 is returned to the initial position and then projection data of the subject 30 in 320 slice planes in order of Z=Z1 to Z=Z64, Z=Z65 to Z=Z128, and so on, according to the procedure similar to the above. Then, reconstruction is performed by using the foregoing projection data on the basis of the positional information of each pixel in the already-set MPR image sections to generate new MPR image data and display it in a specified region of the display 9. This operation is repeated for a period over which observation of a diagnostic region is required.

According to the first embodiment, second projection data is extracted from the first projection data acquired for the subject 30 and then MPR image sections are set from the positioning image data generated from the second projection data. Reconstruction is performed only for the pixels on the MPR image sections by using the first projection data. Briefly, the reconstruction is performed only for the portions necessary for generating MPR images. Therefore, high-resolution MPR image data can be generated by a small number of processing steps.

Since positional information on preset MPR image sections can be used repeatedly to generate MPR image data continuously for the same diagnostic region, a load on the operator can be reduced.

In the foregoing embodiment, projection data is acquired by moving the X-ray detector 16 having two-dimensional X-ray detecting elements 51 stepwise along the body axis of the subject 30 while rotating it. Alternately, the X-ray detector 16 may be rotated helically and continuously to acquire projection data.

The foregoing positioning image data is used to set MPR image sections and so high-resolution images are not required. Accordingly, the pixel size of the positioning image data can be larger than that of the MPR image data.

As has been described, in order to generate a three-dimensional image (an MPR image, a surface image, and a pseudo-endoscopic image), axial images with a necessary slice thickness and slice number for the entire relational region are needed. However, it is merely a part of each axial image that is used in practice to produce the three-dimensional image. Accordingly, particularly in a system in which the three-dimensional image is displayed in real time with the progress of scanning (the three-dimensional image is thickened with the progress of helical scanning), a system in which images after 3D processing (MPR image display in the oblique plane etc.) are displayed (seen through) in real time by multiple-row CT, or a system in which image data is generated in every observation and only raw data is stored, all ordinary axial images are reconstructed before three-dimensional processing and as such, most of calculation power for reconstruction has been wasted.

According to the embodiment, conditions of observation of the necessary three-dimensional image are designated by means such as a low-resolution image (a positioning image) and a necessary-image calculation unit calculates a portion in each axial image necessary for generating finally necessary images and transmits them to the reconstruction arithmetic circuit 21. The reconstruction arithmetic circuit 21 performs reconstruction (back projection) only for the portions and provides the images to the image-data processing circuit 24 having a three-dimensional processing function. The image-data processing circuit 24 generates a three-dimensional image by the same method as the current method. Thus, the operation amount necessary for reconstruction can be reduced while maintaining image quality equal to that by the current method. The method is particularly effective for a system in which reconstruction is performed by a general purpose CPU.

As shown in FIG. 13, the portion 70 for the image in the oblique section 65 is specified on each axial image (slice plane) 71 before the axial images are reconstructed. When the axial images are reconstructed, only the portions 70 are subjected to reconstruction and which are supplied to the image-data processing circuit 24 having the MPR processing function. This remarkably reduces the calculation amount at reconstructing the axial images.

Figure 14:
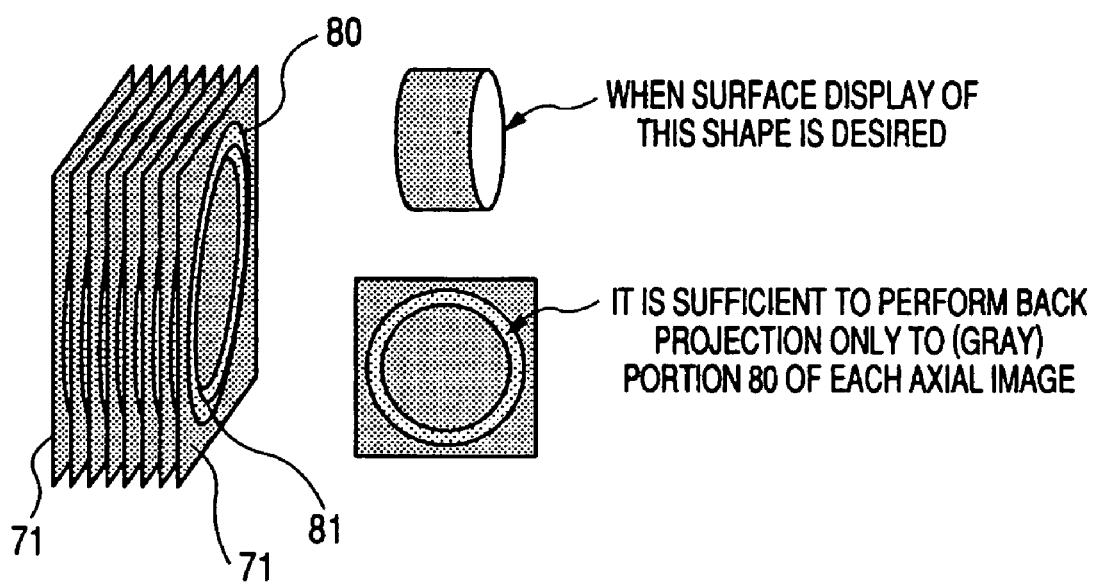
FIG. 14 is a diagram of a reconstruction position (region to be reconstructed) corresponding to the three-dimensional plane in the embodiment.

The embodiment can also be applied to a surface image, as shown in FIG. 14. Before reconstructing axial images, a portion 80 intersecting a surface 81 on each slice plane 71 is specified by using a roughly reconstructed image etc. When reconstructing axial images used in three-dimensional processing, only the portion 80 is reconstructed and which is used as input data for three-dimensional processing. Thus, the operation amount at reconstructing the axial image can be reduced greatly as in the case above.

(Second Embodiment)

A second embodiment of the present invention will be described. The second embodiment is characterized in that projection data in multiple slice planes are acquired continuously, with the relative position between the subject 30 and the frame rotating unit 2 fixed with respect to the body axis (Z-direction) of the subject 30 and the generation and display of MPR image data in a desired section are performed by using the acquired data.

(Procedure for Generating MPR Image Data)

Figure 9:
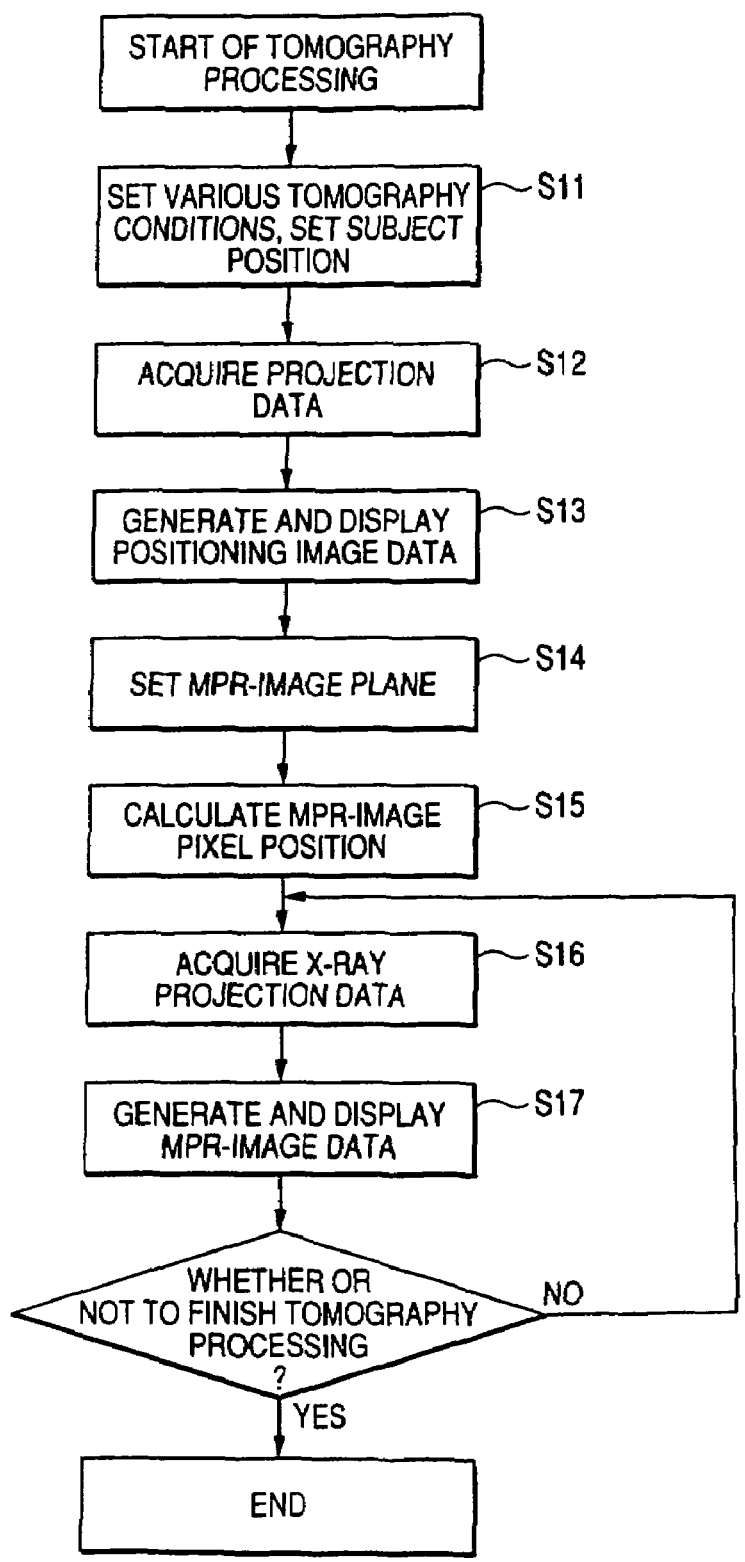
FIG. 9 is a flowchart for the procedure of generating MPR image data according to a second embodiment of the invention.

Since the structure of the X-ray CT scanner 100 according to this embodiment is the same as that of the first embodiment, its description will be omitted here. The procedure for instantly generating MPR image data will be described using the flowchart shown in FIG. 9. The operator first sets projection-data acquisition conditions, reconstruction conditions, image display conditions, etc. with the input unit 10. Then, the operator places the subject 30 on the tabletop of the bed 1 and moves it along the body axis so that the subject 30 is placed in the position of a specified slice plane determined by the X-ray tube 13 and the X-ray detector 16 (step S11).

Figure 10:
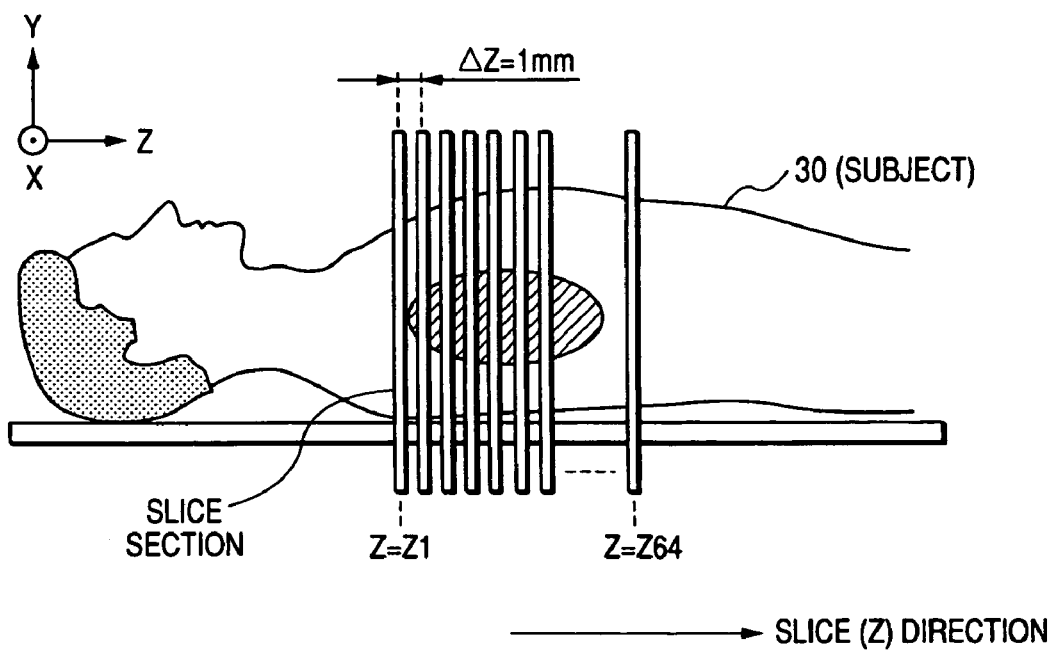
FIG. 10 is a diagram showing a method for acquiring projection data in the embodiment.

FIG. 10 shows a method for acquiring projection data according to this embodiment. This embodiment uses the X-ray detector 16 having 64 equivalent elements in the slice direction, in which projection data in 64 slice planes are acquired with the X-ray detector 16 fixed in the slice direction (along the body axis). For example, the X-ray detector 16 having the X-ray detecting elements 51 disposed at intervals of 1 mm in the slice direction is rotated around the subject 30 to detect X-rays emitted from the X-ray tube 13, so that projection data in slice positions Z1 to Z64 with slice intervals $\Delta Z1$ of 1 mm are acquired.

The operator inputs command signals for acquiring projection data and generating and displaying positioning image data with the input unit 10. The system controller 11 which has received the command signals from the input unit 10 sends a control signal to the bed•frame mechanism 3 via the mechanism controller 4 to rotate the frame rotating unit 2 around the subject 30, thereby acquiring projection data.

At X-ray application to the subject 30, the high-voltage generator 12 supplies the X-ray tube 13 with power (tube voltage and tube current) necessary for applying X-rays, thus applying fan-beam X-rays toward the subject 30. The X-rays that have passed through the subject 30 are detected by the X-ray detector 16 of the projection-data acquisition unit 6. The application of X-rays to the subject 30 and detection of X-ray transmission data are performed while the X-ray tube 13 and the X-ray detector 16 are being rotated around the subject 30. The detected X-ray transmission data is stored as projection data in the projection-data storage circuit 20 via the switch group 17, the DAS 18, and the data transmission circuit 19 (step S12).

Upon completion of acquisition of projection data for 64 slices, the system controller 11 provides the reconstruction arithmetic circuit 21 with positional information of the slice positions Z=Z8, Z16, . . . Z64, which are set at, e.g., slice intervals of $\Delta Z2$=8 mm. The reconstruction arithmetic circuit 21 then reads projection data corresponding to the slice positions Z=Z8, Z16, . . . Z64 in the range of, e.g., 180 degrees+the fan-beam angle from the projection data with slice intervals $\Delta Z1$ of 1 mm which are stored in the projection-data storage circuit 20, thereby performing reconstruction. The generated multiple (eight) two-dimensional positioning images are then stored in the image-data storage circuit 22.

The image-data processing circuit 24 reads the eight two-dimensional positioning images from the image-data storage circuit 22. The eight two-dimensional positioning image data are interpolated in the slice direction and combined and are further subjected to volume rendering to generate three-dimensional positioning image data in which the body surface and the boundary surface of organs are highlighted. The generated three-dimensional positioning image data is stored in the image-data storage circuit 22 and displayed on the monitor 28 of the display 9 (step S13).

The operator then sets a section for an MPR image for the three dimensional positioning image displayed on the display 9 (step S14). The reconstruction-region calculation circuit 23 calculates the positions of all pixels that construct the MPR image section set for the three-dimensional positioning image 61 and stores their positional information in the internal storage circuit (step S15). Briefly, the reconstruction-region calculation circuit 23 specifies 64 portions where the 64 slice planes in which data are acquired and the set section intersect each other.

When the positions of multiple pixels (multiple portions) on the MPR image section are specified according to the foregoing procedure, the operator inputs command signals for generating and displaying MPR image data with the input unit 10. The system controller 11 which has received the command signals from the input unit 10 acquires projection data in Z=Z1 to Z64 by the same way as the above and stores the acquired projection data in the projection-data storage circuit 20 (step S16).

The reconstruction arithmetic circuit 21 reads the positional information on the MPR image section and the pixels stored in the reconstruction-region calculation circuit 23 and the projection data stored in the projection-data storage circuit 20. Then each pixel in the MPR image section is reconstructed by using the projection data to generate MPR image data and which are stored in the image-data storage circuit 22.

The display-data generating circuit 26 of the display 9 reads the MPR image data stored in the image-data storage circuit 22 and generates display image data in accordance with a specified display format. The display image data is subjected to D/A conversion and TV-format conversion by the converter circuit 27 and is then displayed on the monitor 28 (step S17).

The rotation of the frame rotating unit 2 and the acquisition of projection data by the X-ray tube 13 and the projection-data acquisition unit 6 mounted to the frame rotating unit 2 are performed continuously. The generation and display of the MPR image data are then performed continuously using the acquired projection data and according to the positional information of the preset MPR image section.

When the position of the MPR image section must be changed, the operator inputs a command to change the MPR image section to return to the setting of the MPR image section in step S14. Specifically, the monitor 28 of the display 9 again displays the three-dimensional positioning image to which the MPR image section is added and so the operator changes the MPR image section to a desired position using the input device of the input unit 10. In that case, the setting of the MPR image section and the generation and display of the MPR image data can be performed in a very short time. Therefore, the operator can set the position of the desired MPR image section while observing the MPR image displayed on the monitor 28. In such a case, it is preferable to display the MPR image and the three-dimensional positioning image to which the MPR image section is added in parallel, as shown in FIG. 8.

According to the second embodiment, projection data are acquired in multiple slice planes in the diagnostic region of the subject and the position of the MPR image section is set for the positioning image obtained from the projection data. The projection data acquired for the same diagnostic region continuously are reconstructed according to the positional information of the MPR image section, so that the MPR image in the diagnostic region can be displayed in real time.

Since also the change of the MPR image section can be performed while the real-time MPR image is being observed, an optimum MPR image section for the diagnostic region can be set accurately in a short time. This increases diagnostic efficiency and greatly reduces a load on the operator.

In the second embodiment, the positioning image data and the first MPR image data may be generated according to the same projection data, as in the first embodiment. When the projection data acquired at generating the positioning image data are not used to generate the MPR image data, as in the second embodiment, the projection data may be acquired at slice intervals ($\Delta Z2$) larger than those of the projection data used to generate the MPR image data.

Although the invention has been described in its preferred embodiments, it is to be understood that the invention is not limited to those but modifications may be made. For example, according to the embodiments, the pixels of the MPR image in slice planes orthogonal to the body axis of the subject 30 are reconstructed using projection data acquired by scanning the slice planes. The reconstruction may be made using projection data in three-dimensional space.

Figure 11:
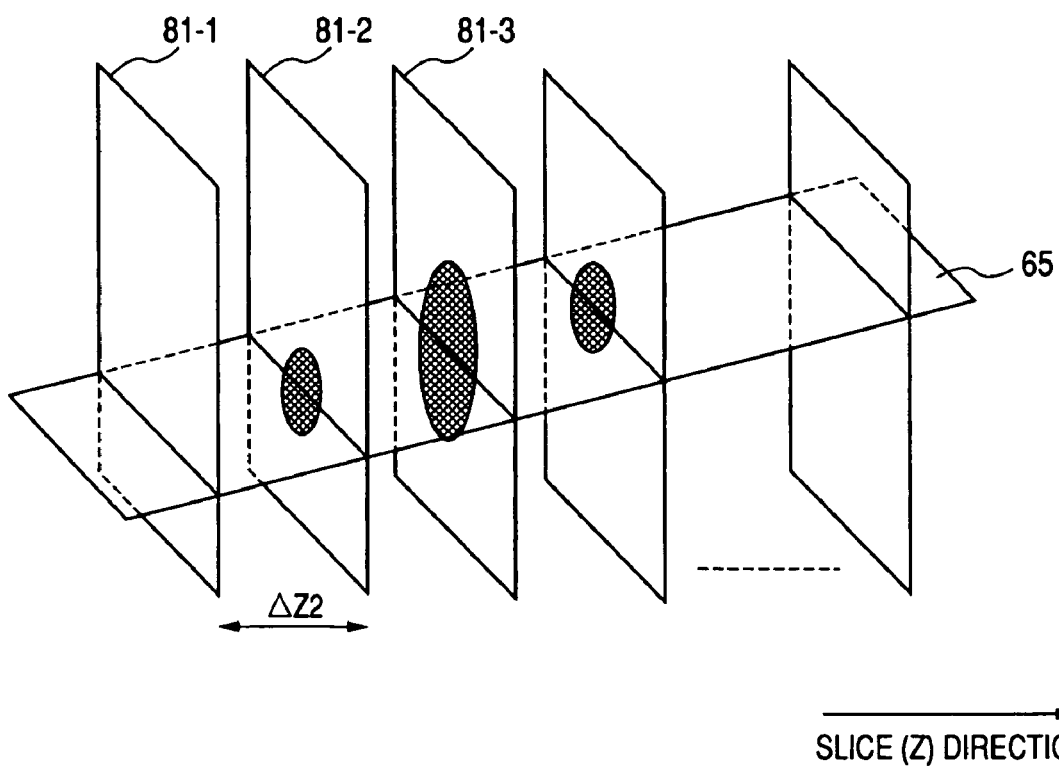
FIG. 11 is a diagram showing a modification of the method for displaying positioning images according to the first and second embodiments of the invention.

According to the embodiments, a three-dimensional positioning image acquired by volume-rendering two-dimensional positioning image data is used as the positioning image for setting an MPR image section. However, the invention is not limited to that. For example, as shown in FIG. 11, the MPR image section may be set in such a manner that two-dimensional positioning images 81-1, 81-2, 81-3 and so on which are generated at slice intervals of $\Delta Z2$ are arranged in three dimensions on the monitor 28 of the display 9 and the combination of the two-dimensional positioning images and the oblique section 65 are displayed.

Although the invention has been described in the case in which the projection data used for generating the positioning image data and the MPR image data are acquired or extracted at regular intervals in the slice direction, they may be arranged at irregular intervals. The resolution of the MPR image in the slice direction and the exposure region can be optimized by the "data bundling" by the projection-data acquisition unit 6.

Although the invention has been described as related to the embodiments using the third-generation CT scanner, it is not limited to that but may be applied to other generation CT scanners such as fourth-generation CT scanners.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT scanner comprising:
    a device configured to acquire projection data for a three-dimensional region of a subject;
    an extracting device configured to extract projection data of a plurality of specified slice planes partially from the acquired projection data for the three-dimensional region of the subject;
    a positioning-image generation device configured to generate a plurality of positioning images at intervals on the basis of the extracted projection data;
    a display device configured to display the positioning images;
    a section setting device configured to set a section in a desired direction intersecting the displayed positioning images in accordance with an instruction of an operator;
    a device configured to specify a plurality of partial reconstruction portions at intervals in regions in the vicinity of where said positioning images intersect the set section;
    a device configured to generate a plurality of partial images for the plurality of partial reconstruction portions on the basis of the acquired projection data; and
    a device configured to generate an image for the section on the basis of the plurality of partial images,
    wherein the plurality of positioning images are arranged at intervals larger than those of the plurality of partial images.

2. The X-ray CT scanner according to claim 1, wherein the plurality of positioning images substantially intersect a body axis of the subject at right angles.

3. The X-ray CT scanner according to claim 2, wherein the partial image is a part of the reconstruction plane that substantially intersects the body axis of the subject at right angles.

4. The X-ray CT scanner according to claim 1, wherein:
    the interval between the partial images is equal to a slice pitch for acquiring the projection data; and
    the interval between the positioning images is an integer multiple of the slice pitch, or at least twice as large as the slice pitch.

5. The X-ray CT scanner according to claim 1, further comprising a device configured to generate a three-dimensional image from the plurality of positioning images.

6. The X-ray CT scanner according to claim 5, wherein the three-dimensional image is generated by volume rendering.

7. An image generation apparatus comprising:
    a positioning-image generation device configured to generate a plurality of positioning images at intervals on the basis of projection data partially extracted from a plurality of projection data for a three-dimensional region of a subject;
    a display device configured to display the positioning images;
    a section setting device configured to set a section in a desired direction intersecting the displayed positioning images in accordance with the instruction of an operator;
    a device configured to specify a plurality of partial reconstruction portions at intervals in portions of the three-dimensional region of interest intersecting the set section;
    a device configured to generate a plurality of partial images for the plurality of partial reconstruction portions on the basis of the plurality of projection data for the three-dimensional region of the subject; and
    a device configured to generate an image for the section on the basis of the plurality of partial images,
    wherein the plurality of positioning images are arranged at intervals larger than those of the plurality of partial images.

8. A method for generating image data, comprising the steps of:
    extracting projection data of at least one specified slice plane from the projection data in the plurality of slice planes for the subject;
    generating a plurality of positioning images at intervals on the basis of the extracted projection data;

displaying the plurality of positioning images;

specifying a plurality of partial reconstruction portions at intervals in portions of the three-dimensional region of interest intersecting a section set in a desired direction on the displayed positioning image;

reconstructing a plurality of partial images for the plurality of reconstruction portions on the basis of the acquired projection data; and generating an image for the set section from the plurality of reconstructed partial images, wherein the plurality of positioning images are generated at intervals larger than those of the plurality of partial images.

9. The X-ray CT scanner according to claim 1, wherein the section is a two-dimensional section.

10. The image generation apparatus according to claim 7, wherein the section is a two-dimensional section.

11. The method for generating image data according to claim 8, wherein the section is a two-dimensional section.

* * * * *